United States Patent
Carlson et al.

(10) Patent No.: US 7,262,222 B2
(45) Date of Patent: Aug. 28, 2007

(54) SYNERGISTIC MIXTURES OF O-PHENYLPHENOL AND OTHER NITROGEN AND ALDEHYDE MICROBIOCIDES

(75) Inventors: Paul E. Carlson, Pittsburgh, PA (US); H. Edwin Nehus, Pittsburgh, PA (US)

(73) Assignee: Verichem, Inc., Pittsburgh, PA (US)

( * ) Notice: Subject to any disclaimer, the term of this patent is extended or adjusted under 35 U.S.C. 154(b) by 391 days.

(21) Appl. No.: 10/345,797

(22) Filed: Jan. 16, 2003

(65) Prior Publication Data

US 2003/0196968 A1 Oct. 23, 2003

Related U.S. Application Data

(60) Provisional application No. 60/349,636, filed on Jan. 17, 2002.

(51) Int. Cl.
*A01N 37/52* (2006.01)
*A01N 31/08* (2006.01)
*A61K 31/155* (2006.01)
*A61K 31/05* (2006.01)
*C02F 1/50* (2006.01)

(52) U.S. Cl. .................. 514/634; 514/736; 210/764
(58) Field of Classification Search ............... 514/634, 514/565, 736; 210/764
See application file for complete search history.

(56) References Cited

U.S. PATENT DOCUMENTS

| | | | | |
|---|---|---|---|---|
| 3,917,850 A | * | 11/1975 | Boucher | 514/705 |
| 4,157,977 A | | 6/1979 | Dewar et al. | |
| 4,324,799 A | * | 4/1982 | Koch et al. | 514/471 |
| 4,366,170 A | | 12/1982 | Engelhart et al. | |
| 4,397,851 A | | 8/1983 | Engelhart et al. | |
| 4,442,122 A | | 4/1984 | Engelhart et al. | |
| 4,496,581 A | | 1/1985 | Engelhart et al. | |
| 4,601,954 A | * | 7/1986 | Coleman | 428/522 |
| 4,675,327 A | * | 6/1987 | Fredrick | 514/383 |
| 4,983,618 A | | 1/1991 | Pulido et al. | |
| 5,114,978 A | | 5/1992 | Corti et al. | |
| 5,147,884 A | * | 9/1992 | Diehl et al. | 514/365 |
| 5,266,218 A | | 11/1993 | Roe et al. | |
| 5,284,875 A | * | 2/1994 | Martin | 514/643 |
| 5,403,864 A | | 4/1995 | Bruch et al. | |
| 5,439,681 A | | 8/1995 | Khan et al. | |
| 5,464,851 A | * | 11/1995 | Morpeth | 514/313 |
| 5,585,407 A | * | 12/1996 | Patel et al. | 514/772.6 |
| 5,631,274 A | * | 5/1997 | Austin et al. | 514/397 |
| 5,767,137 A | | 6/1998 | Uhr et al. | |
| 5,798,325 A | | 8/1998 | Beleck | |
| 5,990,174 A | * | 11/1999 | Henry | 514/635 |
| 6,096,225 A | * | 8/2000 | Yang et al. | 210/755 |
| 6,114,173 A | | 9/2000 | Zelmanovic et al. | |
| 6,160,126 A | * | 12/2000 | Kando et al. | 548/477 |
| 6,379,720 B1 | * | 4/2002 | Cooper et al. | 424/778 |

FOREIGN PATENT DOCUMENTS

DE    4317844 A1 * 12/1994

OTHER PUBLICATIONS

D'Ercole, S., Catamo, G., DeFazio, P., Piccolomini, R., "In vitro Antimicrobial Activity of glutaraldehyde plus o-phenylphenol Association (Ratio 2:1)," Minerva Stomatologica, vol. 51 (1-2), Jan. 2002, pp. 29-33.*
Izzat. I.N., Bennett, E.O., "The Potentiation of the Antimicrobial Activities of Cutting Fluid Preservatives by EDTA," ASLE Trans., vol. N. 78-AM-5A-3, Apr. 17, 1978, p. 8.*
Miner, N.A., Ross, C., "Clinical Evaluation of ColdSpore, a Glutaraldehyde-Phenolic Disinfectant," Respiratory Care, vol. 36(2), Feb. 1991, pp. 104-109.*

* cited by examiner

*Primary Examiner*—John Pak
(74) *Attorney, Agent, or Firm*—Beck & Thomas, P.C.

(57) ABSTRACT

Ortho phenylphenol or its sodium salt is shown to form synergistic antimicrobial mixtures with nitrogen and aldehyde-containing microbiocides.

6 Claims, No Drawings

SYNERGISTIC MIXTURES OF O-PHENYLPHENOL AND OTHER NITROGEN AND ALDEHYDE MICROBIOCIDES

RELATED APPLICATION

This application claims the full benefit of Provisional Application No. 60/349,636 filed Jan. 17, 2002.

TECHNICAL FIELD

This invention relates to synergistic mixtures of o-phenylphenol and/or its sodium salt with glutaraldehyde and/or nitrogen-containing microbiocides (antimicrobials) and the use of the synergistic combinations in industrial applications.

BACKGROUND AND INVENTION

O-phenylphenol and Sodium orthophenylphenate (separately or collectively sometimes herein known as "OPP", orthophenolphenol or o-phenylphenol and/or its sodium salt) are known and used extensively as antimicrobial agents in various industrial applications such as preservation of various materials including paints and adhesives as well as to control unwanted microorganisms found in various process waters such as cooling water, paper mills and petroleum production process waters.

The contamination of various products with microbiological growth has led to the study and application of large classes of preservatives, antimicrobial compositions, and microbiocides to inhibit or prevent such contamination. Industrial process waters also have been studied and treated extensively. Preservatives are used in a broad range of products including but not limited to adhesives, cosmetics and toiletries, disinfectants and sanitizers, leather, metal-working fluids, paints and coatings, plastics and resins, latex polymers, textiles and wood. Failure to preserve these products adequately will result in spoilage and loss of the materials to be preserved and will result in an economic loss. Similarly, microbiological growths can have dire consequences if process waters are not adequately treated. Process waters include but are not limited to: industrial recirculating water, paper products (i.e., paper), petroleum production and leather tanning. Process waters are of concern because when fouled with biofilms that develop from the indigenous microbes present, bioflims may develop into thick gelatinous like masses. Slime is produced by a wide range of bacteria, fungi, and yeast. Slime will interfere with the process resulting in a loss of heat transfer, corrosion and fouling.

Some of the microorganisms responsible for the extensive economic effects described above have exhibited resilient resistant tendencies against the standard and widely used microbiocides and antimicrobial compositions, and accordingly the search for more effective antimicrobials has extended to a search for synergistic combinations of materials considered to be relatively safe for humans. There remains a need for combinations of materials of low or nonexistent toxicity to humans which are effective against a wide range of microorganisms.

SUMMARY OF THE INVENTION

This invention includes synergistic ratios of aqueous suspensions of orthophenylphenol or Sodium orthophenylphenate with the following chemical classes: nitrogen-containing antimicrobial compounds and aldehyde-containing antimicrobial compounds. Generally, any ratio of OPP to the other antimicrobial within the range of 1%-99% to 99%-1% by weight will be effective to some degree, but we prefer to use the most efficient combinations, which may be much wider, as seen below. We have found that mixtures of o-phenylphenol with aldehydes and nitrogen-containing antimicrobials can demonstrate synergistic effects as compared to either of the two ingredients used separately against mixed cultures of gram positive and gram negative organisms.

Nitrogen-containing compounds include but are not limited to the following:
1-(3-chloroallyl)-3,5,7-triaza-1-azoniaadamantane, dodecylguanidine acetate, dodecylguanidine hydrochloride, n-alkyldimethylbenzyl ammonium chloride, dialkyl dimethyl ammonium chloride.

Aldehyde antimicrobial compounds include but are not limited to formaldehyde and glutaraldehyde.

DETAILED DESCRIPTION OF THE INVENTION

Orthophenyiphenol was tested in combination known antimicrobial nitrogen-containing compounds and aldehydes. The synergistic blends were determined using a dose protocol. The combinations were evaluated in synthetic white water with pH values of 5.5 and 8.0. The materials were tested against an artificial bacterial consortium containing approximately equal numbers of six bacterial strains. Although the test strains are representative of organisms present in paper mill systems, the effect is not limited to these bacteria. Two of the strains were Kiebsiella pneumoia (ATCC 13883) and Pseudomonas aeruginosa (ATCC 15442). The other four strains were isolated from papermill systems and have been identified as *Curtobacterium flaccumfaciens, Burkhlderia cepacia, Bacillus maroccanus*, and *Pseudomonas glethei*. Each strain was inoculated at 37° C. overnight, then suspended in sterile saline. Equal volumes of each strain were then combined to prepare the consortium. The bacterial consortium was distributed into the wells of a microliter plate in the presence or absence of various concentrations of the active materials. The microliter plates were incubated at 37° C. Optical density (O.D.) readings at 650 nm were taken initially ($t_0$) and after time 4 hours ($t_4$) of incubation.

The raw data was converted to "bacterial growth inhibition percentages" according to the following formula:

$$\% \text{ Inhibition} = [(a-b) \div a] \cdot 100$$

where:
$a = $ (O.D. of control at $t_n$) − (O.D. of control at $t_0$)
$b = $ (O.D. of treatment at $t_n$) − (O.D. of treatment at $t_0$)

The inhibition values can be plotted versus dosage for each active and the particular blend. This results in a dose response curve from which the dosage to yield 50% inhibition ($1_{50}$) can be calculated. In the examples (tables) below, the $1_{50}$ values are expressed as parts per million (ppm) of active material.

The synergism index (SI) was calculated by the equations described by F. C. Kull, P. C. Eisman, H. D. Sylwestrowicz, and R. L. Mayer (1961), Applied Microbiology 9,538-541. The values are based on the amount needed to achieve a specified end point. The end point selected for these studies was 50% inhibition of bacterial growth.

$$\text{Synergy Index } (SI) = (QA \div Qa) + (QB \div Qb)$$

where:
QA=quantity of compound A in mixture, producing the end point
Qa=quantity of compound $A_1$ acting alone, producing the end point
QB=quantity of compound B in mixture, producing the end point
Qb=quantity of compound $B_1$ acting alone, producing the end point If SI is less than 1, synergism exists; if SI is greater than 1, antagonism exists, if SI is equal to 1, an additive effect exists.

Nitrogen compounds form synergistic blends with OPP. To test the hypothesis the following examples of the class were tested: dodecylguanidine HCl, dialkyl dimethyl ammonium chloride. As is known in the art, the N-alkyl dimethyl benzyl ammonium chloride is commonly a mixture of quaternary ammonium compounds wherein the alkyl group may comprise an alkyl group of 10 to 20 carbon atoms. The synergistic activity can be found in examples 1 through 3.

EXAMPLE 1

This example shows synergistic activity between OPP and dodecylguanidine hydrochloride when fed simultaneously in a bacterial consortium in synthetic white water at pH 5.5 and 8.0.

DGH* & NaOPP @ pH 5.5

| ppm DGH | ppm NaOPP | Ratio DGH:NaOPP | Synergy Index |
|---|---|---|---|
| 1.75 | 0.00 | 100 : 0 | 1.00 |
| 2.11 | 3.91 | 1.0 : 1.8 | 1.23 |
| 2.03 | 7.81 | 1.0 : 3.8 | 1.21 |
| 1.88 | 15.63 | 1.0 : 8.3 | 1.17 |
| 1.67 | 31.25 | 1.0 : 18.7 | 1.15 |
| 1.25 | 61.07 | 1.0 : 48.9 | 1.09 |
| 1.26 | 62.50 | 1.0 : 49.6 | 1.10 |
| 0.63 | 102.81 | 1.0 : 164.5 | 0.98 |
| 0.31 | 119.42 | 1.0 : 382.1 | 0.91 |
| 0.16 | 124.01 | 1.0 : 793.7 | 0.85 |
| 0.08 | 166.72 | 1.0 : 2134.0 | 1.06 |
| 0.04 | 179.85 | 1.0 : 4604.1 | 1.12 |
| 0.02 | 169.95 | 1.0 : 8701.5 | 1.05 |
| 0.01 | 176.28 | 1.0 : 18051.1 | 1.08 |
| 0.00 | 163.91 | 0 : 100 | 1.00 |

DGH* & NaOPP @ pH 8.0

| ppm DGH | ppm NaOPP | Ratio DGH:NaOPP | Synergy Index |
|---|---|---|---|
| 2.93 | 0.00 | 100 : 0 | 1.00 |
| 3.12 | 3.91 | 1.0 : 1.3 | 1.11 |
| 3.33 | 7.81 | 1.0 : 2.3 | 1.23 |
| 2.94 | 15.63 | 1.0 : 5.3 | 1.20 |
| 2.50 | 22.91 | 1.0 : 9.2 | 1.14 |
| 2.18 | 31.25 | 1.0 : 14.3 | 1.13 |
| 1.25 | 61.03 | 1.0 : 48.8 | 1.18 |
| 0.91 | 62.50 | 1.0 : 68.8 | 1.08 |
| 0.63 | 79.27 | 1.0 : 126.8 | 1.20 |
| 0.31 | 107.39 | 1.0 : 343.6 | 1.44 |
| 0.16 | 84.52 | 1.0 : 541.0 | 1.10 |
| 0.08 | 85.17 | 1.0 : 1090.2 | 1.08 |
| 0.039 | 85.462 | 1.0 : 2187.8 | 1.07 |
| 0.020 | 0.020 | 1.0 : 4134.9 | 1.01 |
| 0.01 | 82.98 | 1.0 : 8497.3 | 1.03 |
| 0.00 | 80.74 | 0 : 100 | 1.00 |

*DGH—Dodecylguanidine Hydrochloride

EXAMPLE 2

This example shows synergistic activity between OPP and N-alkyl dimethylbenzyl ammonium chloride when fed simultaneously in a bacterial consortium in synthetic white water at pH 5.5 and 8.0.

ADBAC* & NaOPP @ pH 5.5

| ppm ADBAC | ppm NaOPP | Ratio ADBAC:NaOPP | Synergy Index |
|---|---|---|---|
| 1.88 | 0.00 | 100 : 0 | 1.00 |
| 2.12 | 3.91 | 1.0 : 1.8 | 1.15 |
| 2.11 | 7.81 | 1.0 : 3.7 | 1.17 |
| 2.12 | 15.63 | 1.0 : 7.4 | 1.23 |
| 1.90 | 31.25 | 1.0 : 16.4 | 1.21 |
| 1.38 | 62.50 | 1.0 : 45.4 | 1.12 |
| 1.25 | 101.51 | 1.0 : 81.2 | 1.29 |
| 1.05 | 125.00 | 1.0 : 119.6 | 1.33 |
| 0.63 | 136.01 | 1.0 : 217.6 | 1.17 |
| 0.31 | 160.07 | 1.0 : 512.2 | 1.15 |
| 0.16 | 157.10 | 1.0 : 1005.5 | 1.05 |
| 0.08 | 164.29 | 1.0 : 2102.9 | 1.05 |
| 0.04 | 159.96 | 1.0 : 4094.9 | 1.00 |
| 0.02 | 156.82 | 1.0 : 8029.3 | 0.98 |
| 0.01 | 159.31 | 1.0 : 16313.2 | 0.99 |
| 0.00 | 162.46 | 0 : 100 | 1.00 |

ADBAC* & NaOPP @ pH 8.0

| ppm ADBAC | ppm NaOPP | Ratio ADBAC:NaOPP | Synergy Index |
|---|---|---|---|
| 2.88 | 0.00 | 100 : 0 | 1.00 |
| 3.01 | 3.91 | 1.0 : 1.3 | 1.08 |
| 3.24 | 7.81 | 1.0 : 2.4 | 1.18 |
| 2.98 | 15.63 | 1.0 : 5.3 | 1.14 |
| 2.77 | 31.25 | 1.0 : 11.3 | 1.18 |
| 2.50 | 37.34 | 1.0 : 14.9 | 1.13 |
| 2.07 | 62.50 | 1.0 : 30.1 | 1.15 |
| 1.32 | 125.00 | 1.0 : 94.6 | 1.32 |
| 1.25 | 123.28 | 1.0 : 98.6 | 1.28 |
| 0.63 | 144.58 | 1.0 : 231.3 | 1.21 |
| 0.31 | 143.00 | 1.0 : 457.6 | 1.09 |
| 0.16 | 136.65 | 1.0 : 874.6 | 0.99 |
| 0.078 | 154.75 | 1.0 : 1980.8 | 1.09 |
| 0.039 | 145.36 | 1.0 : 3721.1 | 1.01 |
| 0.020 | 139.67 | 1.0 : 7151.3 | 0.96 |
| 0.010 | 144.49 | 1.0 : 14795.4 | 0.99 |
| 0.00 | 145.96 | 0 : 100 | 1.00 |

*ADBAC—N-Alkyl (60% C14, 30% C16, 5% C12, 5% C18) dimethyl benzyl ammonium chloride

EXAMPLE 3

The example shows synergistic activity between OPP and cis-1-(3-Chioroallyl)-3,5,7-triaza-1-azoniaadamantane when fed simultaneously in a bacterial consortium in synthetic white water at pH 5.5 and 8.0.

| ppm CTAC | ppm NaOPP | Ratio CTAC:NaOPP | Synergy Index |
|---|---|---|---|
| \multicolumn{4}{c}{CTAC* & NaOPP @ pH 5.5} | | | |

| ppm CTAC | ppm NaOPP | Ratio CTAC:NaOPP | Synergy Index |
|---|---|---|---|
| 12.93 | 0.00 | 100 : 0 | 1.00 |
| 12.25 | 3.91 | 1.0 : 0.3 | 1.00 |
| 14.70 | 7.81 | 1.0 : 0.5 | 1.25 |
| 16.21 | 15.63 | 1.0 : 1.0 | 1.48 |
| 12.50 | 18.51 | 1.0 : 1.5 | 1.23 |
| 10.68 | 31.25 | 1.0 : 2.9 | 1.28 |
| 6.25 | 43.80 | 1.0 : 7.0 | 1.11 |
| 3.27 | 62.50 | 1.0 : 19.1 | 1.15 |
| 3.13 | 73.85 | 1.0 : 23.6 | 1.31 |
| 1.56 | 84.36 | 1.0 : 54.0 | 1.34 |
| 0.78 | 84.76 | 1.0 : 108.5 | 1.28 |
| 0.39 | 77.33 | 1.0 : 198.0 | 1.14 |
| 0.20 | 74.14 | 1.0 : 379.6 | 1.08 |
| 0.10 | 71.85 | 1.0 : 735.8 | 1.04 |
| 0.00 | 69.46 | 0 : 100 | 1.00 |

CTAC* & NaOPP @ pH 8.0

| ppm CTAC | ppm NaOPP | Ratio CTAC:NaOPP | Synergy Index |
|---|---|---|---|
| 41.70 | 0.00 | 100 : 0 | 1.00 |
| 45.94 | 3.91 | 1.0 : 0.09 | 1.14 |
| 53.87 | 7.81 | 1.0 : 0.15 | 1.36 |
| 56.13 | 15.63 | 1.0 : 0.28 | 1.49 |
| 53.10 | 31.25 | 1.0 : 0.6 | 1.56 |
| 22.47 | 62.50 | 1.0 : 2.8 | 1.12 |
| 12.50 | 78.59 | 1.0 : 6.3 | 1.03 |
| 6.25 | 95.44 | 1.0 : 15.3 | 1.03 |
| 3.13 | 110.13 | 1.0 : 35.2 | 1.10 |
| 1.56 | 113.57 | 1.0 : 72.7 | 1.09 |
| 0.78 | 102.70 | 1.0 : 131.5 | 0.97 |
| 0.39 | 103.17 | 1.0 : 264.1 | 0.97 |
| 0.20 | 99.45 | 1.0 : 509.2 | 0.93 |
| 0.10 | 99.68 | 1.0 : 1020.7 | 0.93 |
| 0.00 | 107.91 | 0 : 100 | 1.00 |

*CTAC—cis-1-(3-Chloroallyl)-3,5,7-triaza-1-azoniaadamantane chloride

Aldehyde compounds, including formaldehyde, form synergistic blends with OPP. This example shows synergistic activity between OPP and glutaraldehyde when fed simultaneously in a bacterial consortium in synthetic white water at pH 5.5 and 8.0. Results with glutaraldehyde are shown in Example 4.

EXAMPLE 4

GLUT* & NaOPP @ pH 5.5

| ppm GLUT | Ppm NaOPP | Ratio GLUT:NaOPP | Synergy Index |
|---|---|---|---|
| 1.29 | 0.00 | 100 : 0 | 1.00 |
| 1.12 | 3.91 | 1.0 : 3.5 | 0.92 |
| 1.12 | 7.81 | 1.0 : 7.0 | 0.97 |
| 1.02 | 15.63 | 1.0 : 15.3 | 1.00 |
| 0.96 | 31.25 | 1.0 : 32.4 | 1.16 |
| 0.63 | 63.55 | 1.0 : 101.7 | 1.34 |
| 0.54 | 62.50 | 1.0 : 115.5 | 1.26 |
| 0.31 | 71.06 | 1.0 : 227.4 | 1.19 |
| 0.16 | 73.77 | 1.0 : 472.1 | 1.11 |
| 0.08 | 81.38 | 1.0 : 1041.7 | 1.15 |
| 0.04 | 77.21 | 1.0 : 1976.7 | 1.07 |
| 0.00 | 74.58 | 0 : 100 | 1.00 |

GLUT* & NaOPP @ pH 8.0

| ppm GLUT | Ppm NaOPP | Ratio GLUT:NaOPP | Synergy Index |
|---|---|---|---|
| 4.09 | 0.00 | 100 : 0 | 1.00 |
| 4.11 | 3.91 | 1.0 : 1.0 | 1.03 |
| 3.90 | 7.81 | 1.0 : 2.0 | 1.01 |
| 4.37 | 15.63 | 1.0 : 3.6 | 1.19 |
| 4.54 | 31.25 | 1.0 : 6.9 | 1.34 |
| 4.01 | 62.50 | 1.0 : 15.6 | 1.45 |
| 2.50 | 97.39 | 1.0 : 39.0 | 1.34 |
| 1.25 | 121.98 | 1.0 : 97.6 | 1.22 |
| 0.63 | 128.98 | 1.0 : 206.4 | 1.12 |
| 0.31 | 129.52 | 1.0 : 414.5 | 1.05 |
| 0.16 | 132.53 | 1.0 : 848.2 | 1.03 |
| 0.08 | 123.07 | 1.0 : 1575.3 | 0.94 |
| 0.04 | 134.57 | 1.0 : 3445.1 | 1.02 |
| 0.00 | 121.98 | 0 : 100 | 1.00 |

*GLUT—Glutaraldehyde

We claim:

1. An antimicrobial synergistic mixture of orthophenylphenol or its sodium salt and dodecyl guanidine hydrochloride wherein the mixture is determined to be antimicrobial synergistic by having a synergy index of less than 1 in a white water at pH about 5.5.

2. The mixture of claim 1 in a weight radio of dodecyl guanidine hydrochloride to orthophenylphenol or its sodium salt from 1-160 to 1-800.

3. A method of controlling microorganisms in industrial water system comprising:
   a) providing an industrial water system; and
   b) adding an antimicrobial mixture of orthophenylphenol or its sodium salt and dodecyl guanidine hydrochloride to the industrial water system, wherein the mixture is determined to be antimicrobial synergistic by having a synergy index of less than 1 in a white water at pH about 5.5.

4. The method of claim 3 wherein the weight ratio of dodecyl guanidine hydrochloride to orthophenylphenol or its sodium salt is about 1:160 to 1:800.

5. A mixture of dodecyl guanidine hydrochloride and orthophenylphenol or its sodium salt in a ratio of about 1:793.7 that shows antimicrobial synergism when in a industrial water system having a pH of about 5.5.

6. A method of controlling microorganisms in industrial water systems comprising:
   a) providing an industrial water system; and
   b) adding a mixture of dodecyl guanidine hydrochloride and orthophenylphenol or its sodium salt in a ratio of about 1:793.7.

* * * * *

UNITED STATES PATENT AND TRADEMARK OFFICE
CERTIFICATE OF CORRECTION

PATENT NO. : 7,262,222 B2  Page 1 of 1
APPLICATION NO. : 10/345797
DATED : August 28, 2007
INVENTOR(S) : Paul E. Carlson and H. Edwin Nehus It is certified that error appears in the above-identified patent and that said Letters Patent is hereby corrected as shown below:

Column 2, Line 13 cancel "1    -(3    -chloroallyl)" and insert --1-(3-chloroallyl)--

Column 2, Line 23 cancel "Orthophenyiphenol" and insert --Orthophenylphenol--

Column 3, Line 15 cancel "HCl" and insert --HCl--

Column 4, Line 52 cancel "N-Alkyl" and insert --N-alkyl--

Column 4, Line 64 cancel "(3-Chioroallyl)" and insert --(3-Chloroallyl)--

Column 5, Line 37 cancel "1-azoniaadamantane chloride" and insert --1-azoniaadamantane--

Column 6, Line 33 cancel "radio" and insert --ratio--

Signed and Sealed this

Eighteenth Day of March, 2008

JON W. DUDAS
*Director of the United States Patent and Trademark Office*

UNITED STATES PATENT AND TRADEMARK OFFICE
CERTIFICATE OF CORRECTION

PATENT NO. : 7,262,222 B2 Page 1 of 1
APPLICATION NO. : 10/345797
DATED : August 28, 2007
INVENTOR(S) : Paul E. Carlson and H. Edwin Nehus It is certified that error appears in the above-identified patent and that said Letters Patent is hereby corrected as shown below:

Column 2, Line 13 cancel "1 -(3 -chloroallyl)" and insert --1-(3-chloroallyl)--

Column 2, Line 23 cancel "Orthophenyiphenol" and insert --Orthophenylphenol--

Column 3, Line 15 cancel "HCI" and insert --HCl--

Column 4, Line 52 cancel "N-Alkyl" and insert --N-alkyl--

Column 4, Line 64 cancel "(3-Chioroallyl)" and insert --(3-Chloroallyl)--

Column 5, Line 37 cancel "1-azoniaadamantane chloride" and insert --1-azoniaadamantane--

Column 6, Line 33 Claim 2 cancel "radio" and insert --ratio--

Signed and Sealed this

Twenty-fifth Day of March, 2008

JON W. DUDAS
*Director of the United States Patent and Trademark Office*